US009955876B2

(12) United States Patent
Chirife (10) Patent No.: US 9,955,876 B2
(45) Date of Patent: May 1, 2018

(54) DEVICE AND METHOD FOR ASSESSMENT OF LEFT VENTRICULAR EJECTION FRACTION AND OTHER PARAMETERS OF CARDIAC PERFORMANCE (71) Applicant: Raul Chirife, Acassuso (AR)

(72) Inventor: Raul Chirife, Acassuso (AR)

( * ) Notice: Subject to any disclaimer, the term of this patent is extended or adjusted under 35 U.S.C. 154(b) by 0 days. days.

(21) Appl. No.: 15/260,126

(22) Filed: Sep. 8, 2016

(65) Prior Publication Data
US 2018/0070833 A1 Mar. 15, 2018

(51) Int. Cl.
| | |
|---|---|
| *A61B 5/04* | (2006.01) |
| *A61B 5/0205* | (2006.01) |
| *A61B 5/02* | (2006.01) |
| *A61B 5/00* | (2006.01) |
| *A61B 7/04* | (2006.01) |
| *A61N 1/365* | (2006.01) |
| *A61N 1/368* | (2006.01) |
| *A61B 5/0472* | (2006.01) |
| *A61B 5/021* | (2006.01) |
| *A61B 5/024* | (2006.01) |

(52) U.S. Cl.
CPC ........ *A61B 5/0205* (2013.01); *A61B 5/02028* (2013.01); *A61B 5/04017* (2013.01); *A61B 5/0472* (2013.01); *A61B 5/4836* (2013.01); *A61B 5/4839* (2013.01); *A61B 5/686* (2013.01); *A61B 5/7275* (2013.01); *A61B 5/746* (2013.01); *A61B 7/04* (2013.01); *A61N 1/3682* (2013.01); *A61N 1/36585* (2013.01); *A61B 5/024* (2013.01); *A61B 5/02108* (2013.01); *A61B 2505/07* (2013.01)

(58) Field of Classification Search
None
See application file for complete search history.

(56) References Cited

U.S. PATENT DOCUMENTS

| | | | | |
|---|---|---|---|---|
| 4,773,401 A | * | 9/1988 | Citak | A61N 1/36514 607/17 |
| 5,086,776 A | * | 2/1992 | Fowler, Jr. | A61B 5/0205 600/452 |
| 5,674,256 A | * | 10/1997 | Carlson | A61N 1/365 607/17 |

(Continued)

*Primary Examiner* — Brian T Gedeon (57) ABSTRACT

The invention consists of a device and method for the prediction of left ventricular ejection fraction (EF) and other cardiac hemodynamic parameters using systolic time intervals in patients with narrow QRS, right bundle branch block, left bundle branch block, right ventricular and/or left ventricular cardiac pacing and in the presence of arrhythmia, such as atrial fibrillation. The device has three inputs: the ECG, a peripheral pulse and a phonocardiogram. Timing parameters are obtained from these signals to calculate a systolic function index, used for the prediction of ejection fraction. Given the invention's features it would be now possible to assess cardiac performance and specifically left ventricular ejection fraction in ambulatory patients as well as during invasive procedures such as the implant of cardiac rhythm management devices. Also, an implantable embodiment of the invention would allow constant monitoring of cardiac performance, parameter adjustment of cardiac devices and automatic drug infusion.

6 Claims, 7 Drawing Sheets

Software flow chart used to estimate left ventricular ejection fraction.

(56) References Cited

U.S. PATENT DOCUMENTS

| | | | | |
|---|---|---|---|---|
| 5,743,267 A * | 4/1998 | Nikolic | ............... | A61B 5/0028 |
| | | | | 128/903 |
| 7,174,203 B2 * | 2/2007 | Arand | ................... | A61B 5/0402 |
| | | | | 600/513 |
| 7,729,764 B2 * | 6/2010 | Hettrick | ............... | A61N 1/3627 |
| | | | | 607/27 |
| 8,229,557 B2 * | 7/2012 | Patangay | ............ | A61B 5/02028 |
| | | | | 600/509 |
| 8,255,042 B2 * | 8/2012 | MacQuarrie | ............. | A61B 5/02 |
| | | | | 600/481 |
| 9,101,275 B2 * | 8/2015 | Thakur | .................... | A61B 7/04 |
| 9,622,664 B2 * | 4/2017 | An | ...................... | A61B 5/02028 |
| 9,687,565 B2 * | 6/2017 | Johansson | ............. | C07D 471/04 |
| 2008/0269822 A1 * | 10/2008 | Ljungstrom | ............. | A61N 1/08 |
| | | | | 607/18 |
| 2010/0152547 A1 * | 6/2010 | Sterling | ................. | A61B 5/029 |
| | | | | 600/301 |
| 2014/0116442 A1 * | 5/2014 | Martin | .............. | A61M 16/0051 |
| | | | | 128/204.23 |
| 2016/0135697 A1 * | 5/2016 | Rinderknecht | .... | A61B 5/02427 |
| | | | | 600/479 |
| 2017/0188978 A1 * | 7/2017 | Kale | .................... | A61B 5/7278 |

\* cited by examiner

Figure 1. Effect of right ventricular pacing on interventricular delay

Figure 2. Effect of right ventricular pacing on pre-ejection period.

Figure 3. Flow chart of electronic circuitry

Figure 4. Software flow chart used to estimate left ventricular ejection fraction.

Figure 5. Software creen shot showing calculation of ejection fraction

Figure 6. Alternative embodiment of the invention.

Figure 7. Sensitivity and specificity of predicted ejection fraction to discriminate normal vs. heart failure patients.

DEVICE AND METHOD FOR ASSESSMENT OF LEFT VENTRICULAR EJECTION FRACTION AND OTHER PARAMETERS OF CARDIAC PERFORMANCE

BACKGROUND OF THE INVENTION

Field of Invention

This invention relates generally to the field of cardiac diagnostic devices and more particularly to the detection and measurement of left ventricular ejection fraction and other parameters of left ventricular systolic function.

Discussion of Prior Art

Left ventricular ejection fraction (EF) is the ratio between the heart stroke volume (SV) and the end-diastolic volume (EDV) of the same beat. (EF=SV/EDV). It is generally expressed as a percentage ranging from 50% to 75% in normal subjects, that is, without cardiac malfunction. EF is intended to express the value of SV (determinant of cardiac output) corrected for EDV, a marker of preload. Measurement of ejection fraction can be done either by invasive or noninvasive methods. In the former, a special catheter is introduced through an artery to the left ventricular cavity, where a contrast medium is injected during several heart beats, a procedure hereinafter referred to as contrast cine left ventriculography (CineLVG). Said contrast material is opaque to X rays, so when filming the x ray fluoroscopy image of the heart at fast frame rate it offers clear visualization of the left ventricular endocardium (which defines the heart's chamber size) during each of several cardiac cycles, allowing measurement of EDV and end-systolic volume (ESV) for the calculation of ejection fraction. By first calculating SV as the difference between EDV and end-systolic volume (ESV) the final formula of EF=((EDV−ESV)/EDV)*100 can be obtained. For many decades this invasive method has been (and still is) considered the gold standard for a precise assessment of cardiac systolic function. Other non invasive or minimally invasive methods can also be used, such as contrast echocardiography (Echo), multi gated radionuclide ventriculography (RNV) and magnetic resonance imaging (MRI) requiring similar calculations of EDV and ESV to obtain EF, as described above for CineLVG. Sometimes these methods may require intravenous injection of contrast material to enhance visualization of the endocardium, thus making them minimally invasive and not exempt of some risks. Tracing of the contour of the ventricular endocardium is needed to calculate ventricular volumes by using Dodge et al method [1] or the method of discs as described by Simpson, well known in the art. Nevertheless, other problems exist for each of these alternatives: Echo is observer-dependent, that is, the result varies with the expertise of the person doing the study, since the endocardium is traced by hand, and also, in a considerable number of patients it is not possible to obtain images of sufficient quality to accurately assess ventricular volumes and EF. RNV requires the injection of a radioactive contrast material to visualize the LV cavity in a sequence of beats and some degree of operator and equipment-dependence also exists. MRI is far more complex procedure, since standard static images are not adequate. It may also require contrast injection and special software is needed to increase frame rate by interpolation of several beats. Furthermore, it is contraindicated in most patients with pacemakers or implantable defibrillators. In spite of its limitations, Echo with or without contrast is the most frequently used non invasive method to measure EF. It is less expensive and less time-consuming than RNV and MRI. A further problem consists of the low correlation in the values of EF obtained between above methods in the same patients. For example, in previous studies it has been shown considerable discrepancies when comparing them between each other in the same patients. Differences may range between 10% and 20% or more in absolute percentage values. That is, if with one of above methods EF is calculated at 40%, the same patient may show calculated EFs of up to 50% or down to 30%, depending on the method being used[2,3].

EF is a very important parameter in cardiology. For example, it is key to decide the implant of a cardioverter-defibrillator (ICD), it determines eligibility for cardiac resynchronization therapy (CRT) in heart failure patients (Pts) with left bundle branch block (LBBB) (Madit 1 and Madit 2 studies), it may help selecting the optimal left ventricular pacing site of CRT devices at the time of implant by detecting mechanical resynchronization with CRT pacemakers and during follow-up help in device performance optimization. Unfortunately, testing for optimal LV pacing site for these patients is not routinely done in view of the difficulties of doing an Echo study in the catheterization lab or inserting left ventricular leads with manometers to measure LV dP/dt as a marker of cardiac function. These methods, albeit they are valid markers of hemodynamic performance, may augment the risks of complications and significantly extend the duration of the procedure. Failure to identify an optimal LV pacing site may be one of the reasons for failure to respond to CRT in up to 30% of cases. Furthermore, with the advent of endocardial left ventricular pacing with conventional leads or leadless left ventricular pacing (whereby a sub-miniature pacing device is implanted on the endocardium of the left ventricle) require a fast, simple non-invasive method to select the optimal LV pacing site at the time of device implant. Selecting a site with adequate pacing threshold may not suffice, for such place may not provide the optimal mechanical (hemodynamic) response. Therefore, using a simple, precise indicator of an optimally placed LV lead, whether it is via the coronary sinus, left ventricular epicardial or endocardial would be very valuable. In addition to above, measurement of EF and other hemodynamic parameters such as the pre-ejection period and left ventricular ejection time may also allow confirmation of heart failure in patients with equivocal symptoms, as it may happen in patients with anemia or lung disease. It can also be used in the follow-up of cancer patients undergoing chemotherapy that may have cardiac toxicity and to assess the mechanism of syncope during head-up tilt testing. Another application of EF is described in U.S. Pat. No. 5,154,171 where the value of EF, a marker of contractility, is used to adjust pacing rate with an implantable pacemaker. Since other noninvasive or minimally invasive methods are not cost-effective for most of the uses of EF, and Echo is sometimes hampered by technical difficulties, it is evident that the present invention provides an alternative EF calculation method that is noninvasive, easy to use, fast, cost-effective and operator-independent. This would make unnecessary to have within the operating room where a cardiac procedure is taking place, an echocardiogram machine or to use more invasive approaches to test cardiac performance such as measurement of left ventricular dP/dt with indwelling catheters.

Systolic Time Intervals

Systolic time intervals (STI) as known in the prior art include pre-ejection period (PEP), left ventricular ejection time (LVET) and the ratio PEP/LVET and have long be used to assess cardiac performance[4-8]. PEP is the time from the onset of QRS or ventricular pacing pulse to the onset of central aortic flow or pressure. LVET is the time from the onset to the end of aortic pressure or flow and remains without significant changes as the pulse waveform travels along the blood vessels[5]. Systolic time intervals can be non-invasively obtained from recordings of the ECG, a peripheral pulse waveform and heart sounds[4,5,9,10] as surrogates of central measurements. One of the features of the central aortic pressure or flow pulse is that the arterial pulse waveform is not delayed; therefore PEP and LVET are directly measured, and a indication of this is that the dicrotic notch of the pulse is aligned with the aortic component of the second heart sound, both signaling the closure of the aortic valve and the end of ejection. Since an arterial pulse obtained far from the heart is delayed as compared to a tracing obtained in the central aorta, the time from the onset of QRS to the upstroke of the peripheral pulse, representing PEP, is prolonged. This extended PEP is hereinafter referred to as a surrogate of PEP (PEPsu), and its value representing the true PEP plus the pulse transit time (PTT). Since the duration of ejection (LVET, from the foot to the dicrotic notch of the arterial pulse) is not affected by the distance of the arterial pulse from the heart[11], that is, both the foot and the dicrotic notch of the pulse are equally delayed, one way of obtaining the true PEP is by subtracting the value of PTT, from the duration of PEPsu: PEP=PEPsu−PTT (FIG. 1). PEP reflects the duration of ventricular isometric contraction, which in turn is strongly related to left ventricular rate of pressure rise (dP/dt), a marker of contractility. Given this feature of PEP it has been used as a sensor signal for rate-adaptive ventricular pacing[12,13,14], shown in U.S. Pat. No. 4,719,921 and U.S. Pat. No. 5,168,869) and proposed to distinguish physiologic from pathologic tachycardia in U.S. Pat. No. 4,865,036. As mentioned above, LVET requires no correction because peripherally measured values are closely correlated with LVET obtained in the central aorta[11]. LVET is related to stroke volume and for that reason is pre-load dependent, and is modified by heart rate[4,16]. The ratio of both, PEP/LVET (or its reciprocal, LVET/PEP) have been repeatedly shown over many decades that said ratio is very valuable to distinguish degrees of cardiac performance, to separate patients with normal vs. abnormal cardiac function[7], and to detect sub-clinical manifestations of cardiac dysfunction[8]. Although the preferred approach to measure STI is by the traditional method of using ECG, pulse waveform and phonocardiogram, systolic time intervals can also be invasively assessed with pressure sensors, impedance catheters or aortic flow obtained by Doppler.

STI and EF

In the original publication by Garrard, Weissler and Dodge[16] it was shown that EF can be predicted from STI using the following equation: EF=1.125−1.25*PEP/LVET. This regression equation was obtained by comparing the ratio PEP/LVET (Weissler's ratio) with ejection fraction as measured by contrast cine left ventriculography, a gold standard for ventricular volume measurements[1]. It can be observed from the equation that the higher the Weissler ratio, the lower the predicted ejection fraction. Several studies followed thereafter showing high correlations of said ratio with EF[10,17]. However, these studies were done in patients with narrow QRS (that is, without right bundle branch block (RBBB), left bundle branch block (LBBB) or any mode of right and/or left ventricular pacing, therefore severely limiting the use of STI to predict EF in a substantial number of patients. The reason for this is that LBBB and right ventricular pacing extend the duration of PEP because the onset of left ventricular depolarization/contraction is postponed, creating an inter-ventricular delay that alters the PEP/LVET ratio independently from changes in contractility and EF[18]. For example, a patient with a right ventricular pacemaker and normal ejection fraction (≥50% by echocardiography or other methods) will have an abnormally high Weissler ratio by virtue of an extension of PEP (the numerator of the equation) and EF predicted from it will be lower than that observed. Therefore, a universal equation cannot be used for all patients. U.S. Pat. No. 5,086,776 discloses a complex, multi-parameter apparatus and method to predict EF using Garrard's equation but not considering cardiac pacing. Using said equation will yield a lower value of predicted EF in pacemaker patients, since PEP in these patients is longer not because of longer isometric contraction time but due to an artificially prolonged inter-ventricular conduction delay, resulting simply in a late-onset LV contraction as described above.

For the purpose of this invention a large number of patients were studied during sinus rhythm with narrow QRS, during atrio-ventricular (AV) optimization in dual-chamber pacemakers during right ventricular pacing and in patients with cardiac resynchronization therapy (CRT) by recording STI along with a calibrated non invasive recording of the arterial blood pressure (Colin NIBP, Colin Corp, USA) and using a prototype of the invention herein described. The systolic function index (the ratio LVETc/PEPc) obtained in these studies proved superior to arterial blood pressure to detect subtle hemodynamic changes due to AV interval modulation or when switching from biventricular to single-ventricle or no pacing in patients with CRT devices. Additional testing was done in patients with RBBB, LBBB and right ventricular pacing, with and without heart failure. Furthermore, studies using said prototype included regression analysis of SFI vs. EF in patients with LBBB[19], and tests of the ability of SFI to rule-in or rule-out the presence of cardiac malfunction[7].

It is therefore the object of this invention to provide a novel device and method to estimate a patient's left ventricular ejection fraction, calculated from a systolic function index (SFI), as well other parameters of cardiac function, in a wide variety of patients with narrow QRS, RBBB, LBBB, and right ventricular and/or left ventricular pacing. EF estimation with the invention results in a cost-effective, easy to use and operator-independent procedure that would allow evaluation of cardiac performance in ambulatory patients as well intra-operative evaluations or within implantable devices, so far not possible or non-practical.

SUMMARY OF THE INVENTION

This invention utilizes a specially designed apparatus and software for automatic measurement of a set of noninvasive parameters of cardiac function and to obtain what hereinafter is called Systolic Function Index (SFI), from which the left ventricular Ejection Fraction can be predicted. This invention allows prediction of ejection fraction in patients with narrow QRS, bundle branch blocks and a variety of cardiac pacing modalities, unlike prior art that only allow prediction of EF in patients with narrow QRS. The SFI is obtained using measurements of heart rate (HR), QRS duration, PEP, LVET, inter-ventricular delay (IVD) and pulse transit time (PTT) using non-invasive, invasive, external or implantable devices. In order to accomplish the main objects of the invention, a combination of a specific hardware, certain systolic time intervals, definition of a novel systolic function index and dedicated software are used. In a preferred embodiment, only sensors for non invasive measurements were used in the prototype, although similar results may be obtained using invasive means for the detection of ECG, heart sounds and arterial pulse, such as intra-cardiac or thoracic impedance[13], sub-cutaneous photo-densitometry, arterial blood pressure or flow, and other, including implantable devices, such as a DDD pacemaker, a cardioverter-defibrillator, a cardiac resynchronization therapy device or drug infusion apparatus, all with included sensors.

DESCRIPTION OF THE DRAWINGS

FIG. 1. Systolic Time Intervals. The tracing of this figure was obtained with a prototype of this invention, and it illustrates a typical non invasive recording of the ECG, a peripheral pulse and a phonocardiogram. Timing markers for systolic time intervals measurements are also depicted. Heart rate is calculated from QRS to QRS timing cycle time. The pre-ejection period surrogate (PEPsu) is the time from the onset of QRS (in this case a right ventricular paced beat) to the upstroke of the peripheral pulse, which in this example was obtained with a finger photo-plethysmograph. Left ventricular ejection time (LVET) extends from the foot of the peripheral pulse (marker of the onset of ejection) to the dicrotic notch, a marker of the end of ejection. The pulse transit time (PTT) is the time from the aortic component of the second heat sound (S2) to the dicrotic notch, both of which are expected to be aligned, if the tracing had been obtained in the central aorta, with 0 PTT delay.

FIG. 2. Effect of RV Pacing on IVD. Whenever the right ventricle is paced, the left ventricular depolarization and contraction are delayed because the electrical depolarization wavefront follows a longer pathway to reach the left ventricle, thus causing an artificial lengthening of inter-ventricular delay (ND). This phenomenon is expressed in this tracing as a prolongation of PEPsu of the paced beat (third beat from the left) as compared to the PEPsu of a beat with narrow QRS (second beat from the left). In this example, the difference paced PEPsu–sensed PEPsu=IVD=32 ms.

FIG. 4. Software Algorithm. Values of cycle length, PEPsu, LVET, PTT and QRSd are used by the software to normalize LVET to a heart rate of 60 bpm and to compensate PEPsu for PTT and for IVD. IVD during right ventricular pacing is calculated from the duration of QRS using a previously published equation[20]. A systolic function index is calculated, and ejection fraction estimated from it.

FIG. 5. Screenshot of the computer display produced by software. This figure shows the results of a study done on a patient with symptomatic heart failure using the prototype of the invention. The screen displays the actual-real time waveforms of ECG, a marker channel, arterial pulse tracing and phonocardiogram on the upper portion of the screen. To the right of it, one single beat is shown resulting from ensemble averaging of 2 to 8 or more beats, with corresponding landmarks (dotted lines) for the beginning and end of QRS, the foot and dicrotic notch of the pulse waveform and heart sounds. At the lower part of the screen beat-by-beat trends of key measurements is shown. On the upper left, there is a statistics window with average values of the measured parameters and the result of the calculated ejection fraction. The value shown (41%) is below normal, consistent with the patient's heart failure condition.

FIG. 6. Alternative embodiment of the invention. In this embodiment, detection and initial filtering of signals is done by hardware while calculation of ejection fraction and other hemodynamic parameters is done by an external PC or a dedicated microprocessor.

FIG. 7. Sensitivity and specificity of predicted ejection fraction. Two groups of patients were selected and studied using a prototype of the invention. One group consisted of asymptomatic patients with no evidence of heart malfunction and the other with clinical symptoms of heart failure. Ejection fraction was estimated from the SFI and results tested for sensitivity and specificity to rule-in or rule-out cardiac malfunction. Both sensitivity and specificity values are very high[7].

DESCRIPTION OF A PREFERRED EMBODIMENT

Figure 1:
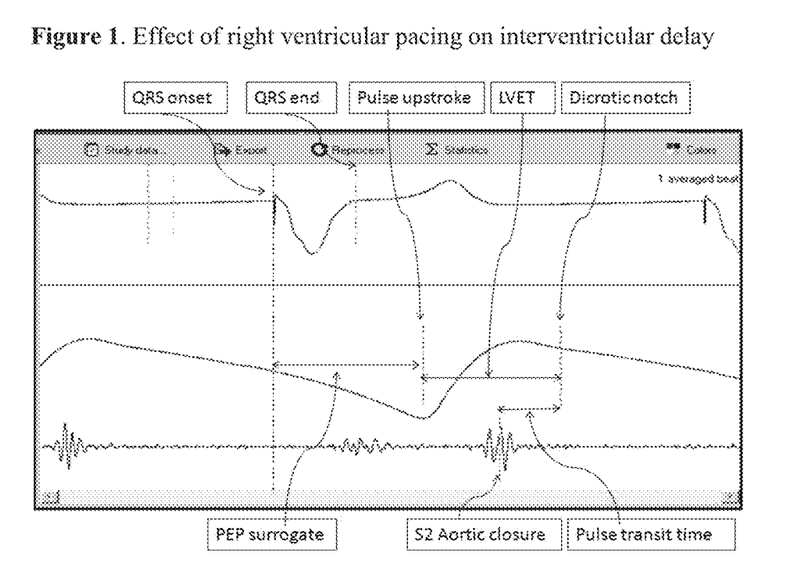
Figure 2:
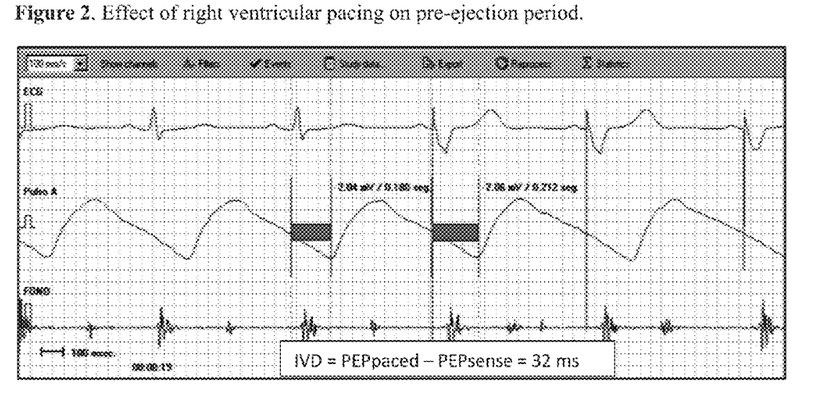

In a preferred embodiment of the invention, estimation of ejection fraction is done using a combination of physiologic parameters and dedicated software. Said physiologic parameters are the so-called systolic time intervals, obtained from a plurality of inputs, such as the ECG, an arterial pulse and a phonocardiogram. In this example, ECG is obtained from three standard disposable electrodes placed in a triangular fashion on the right clavicle, the right costal border and at the mid-clavicular line at the level of the $4^{th}$ inter-costal space. The peripheral pulse is obtained with a commercially available transmittance O2 saturation sensor placed on a finger, although reflectance types are also suitable. The phonocardiogram, is recorded with a commercially available microphone, such as part # Part #: TSD108 from Biopac Systems Inc or similar. The tracings shown in FIGS. 1, 2 and 5 were obtained with the prototype at a sampling rate of 4 KHz for an accurate detection of pacemaker pulses, whenever they are present. Detection of landmarks and automatic measurements of systolic time intervals were obtained by software, shown as trends in FIG. 4, and hereinafter described in detail.

Figure 3:
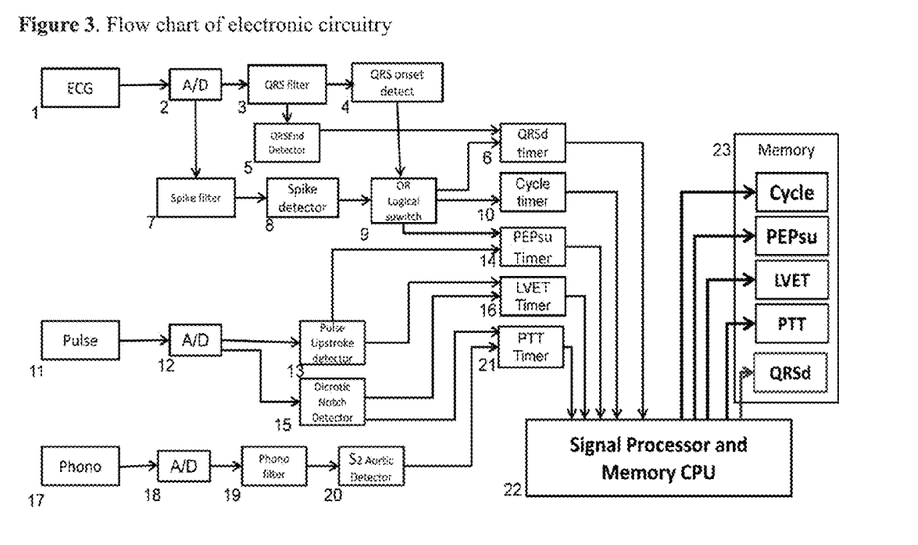
FIG. 3. Electronic algorithm. Flow chart of a preferred embodiment of the invention.

FIG. 3 depicts a preferred electronic circuitry algorithm used in the present embodiment, although other configurations may be equally suitable. The front-end of the device has inputs for above mentioned physiologic signals, namely the ECG, an arterial pulse and the phonocardiogram. The ECG cables 1 are connected to an amplifier and analog to digital converter 2, sampling at 4 Khz to be able to accurately detect pacemaker pulses which could be as short as 0.2 ms in duration. Then the signal is directed to pacemaker spike filter 7 and QRS filter 3 for signal conditioning to remove AC and noise by applying a band-pass between 0.5 to 35 Hz. Said conditioned QRS signal in 3 is then directed to step 4 for QRS onset detection, and simultaneously to QRS end detector 5. Signal from QRS onset detector 4 is directed to logical switch 9. Said logical switch also receives a signal from high-pass spike filter 7 after going through spike detector 8. Logical switch 9 therefore signals the onset of QRS or pacemaker spike, whichever is first to occur and drives the timing signal to QRS duration timer 6, cycle length duration timer 10 and PEPsu timer 14. QRS duration timer 6 calculates QRS duration as the time difference from the onset of intrinsic or paced QRS, whichever occurs first from logical switch 9, to the end of QRS as detected in step 5. Cycle timer 10 calculates cycle length as the timing difference between current and preceding consecutive logical switch 9 outputs. Outputs of QRS duration 6 and Cycle Timer 10 are directed to memory and signal processor CPU 22 for further processing.

Pulse transducer 11 output is fed to analog to digital converter 12 and its output to both pulse upstroke detector 13 and dicrotic notch detector 15, both of which include band-pass digital filters from 6 to 20 Hz. Timing of these outputs are directed to timer 16 for left ventricular ejection time calculation as the difference between them, and value further directed to said memory and signal processor CPU 22. Timing of dicrotic notch detector is also directed to PTT timer 21.

Phonocardiogram signal 17 goes through the analog to digital converter 18, programmable 30-70 Hz band-pass filter 19 and second heart sound detector 20. The object of said detector 20 is to identify the aortic component of the second heart sound; therefore the sound wave vibration of maximum amplitude is detected. The signal output from dicrotic notch detector 15 and aortic second sound detector 20 are fed to PTT timer 21 where pulse transit time is calculated as the timing difference between dicrotic notch detector 15 described above and second heart sound detector 20. Signal from PTT timer is further directed to memory and signal processor CPU 22. 21 to calculate the value of pulse transit time. This interval will be used to correct PEPsu to true PEP. Said memory and signal processor CPU 22 stores Cycle Length, PEPsu, LVET, PTT and QRSd in memory 23 for further calculations according to software algorithm.

Figure 4:
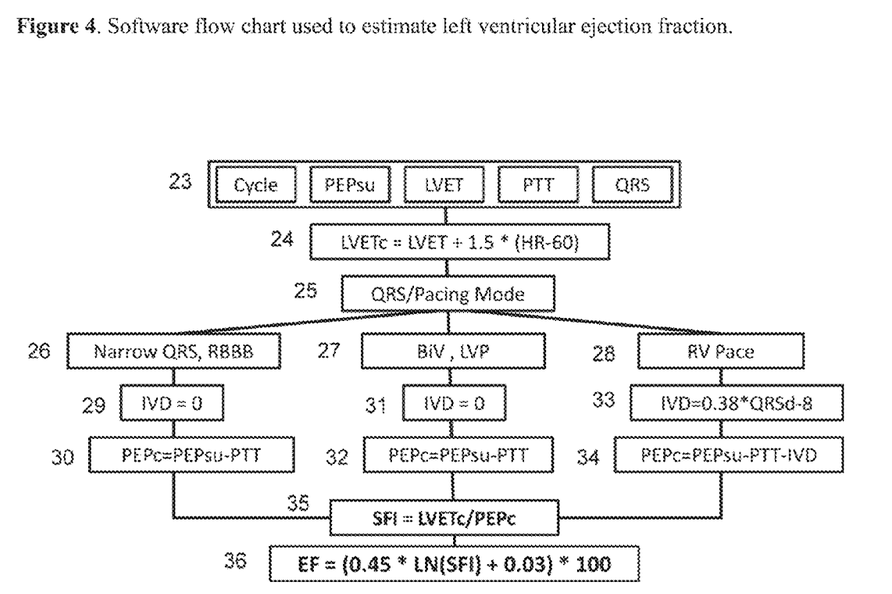
Figure 5:
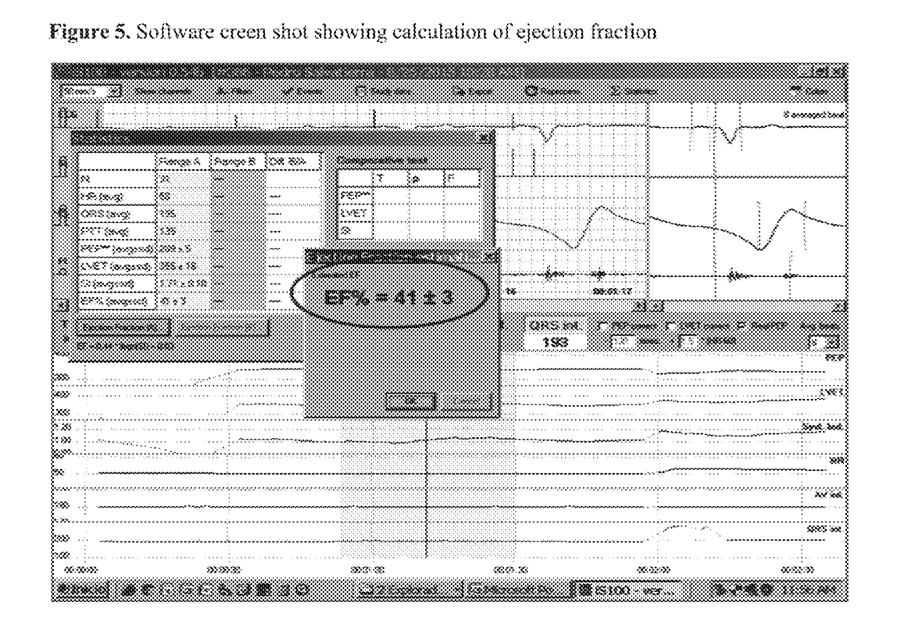

Software Algorithm:

Block diagram is depicted in FIG. 4. Based on data stored by CPU 22 in memory 23, a first step 24 is taken to calculate rate-corrected LVET as: LVETc=LVET+k*(HR-60), where k is the slope of LVET vs. heart rate and which by default 1.5 but could range from 1.0 to 2. If necessary, an actual slope value can be calculated as the ratio between a change in LVET resulting from a change in heart rate, which said heart rate is calculated as HR=60,000/cycle length (in ms). LVET needs to be corrected for heart rate because rate changes affect the duration of LVET, thus altering the systolic function index. Not correcting LVET for rate makes comparisons difficult within the same patient at different heart rates or when compared to other patients. Next, the device operator needs to enter QRS type or pacing mode by selecting one of options 26, 27 or 28. If option 26 for narrow QRS or RBBB is selected, then IVD is considered 0 in 29 and PEPsu is thus only corrected for pulse transit time in 30 as: PEPc=PEPsu-PTT, where PEPc indicates that PEPsu has been fully corrected for the selected QRS type or pacing mode, with 0 IVD. If option 27 for biventricular pacing (BiV) or left ventricular pacing (LVp) is selected IVD is also considered 0 in 31 and PTT correction is done as shown in step 32: PEPc=PEPsu-PTT. Selecting option 28 RVPace (right ventricular pacing) inter-ventricular delay is calculated in 33 as IVD=0.38*QRSd-8, according to previously published equation[20] and PEPc=PEPsu-PTT-IVD in 34. This equation however could be replaced by other calculations aimed at predicting the value of IVD based on QRS total or partial duration or on other cardiac parameters. Once correction of PEPsu for PTT and IVD have been done for each QRS type or pacing modality, calculation of the systolic function index is possible in 35 as: SFI=LVETc/PEPc, which leads to step 36 to calculate ejection fraction as EF=(0.45*LN(SFI)+0.03)*100, where LN(SFI) is the natural logarithm of SFI. This equation is one example of the numerous possible ways EF can be correlated and predicted from the quotient LVETc/PEPc, or its reciprocal, PEPc/LVETc.

Figure 6:
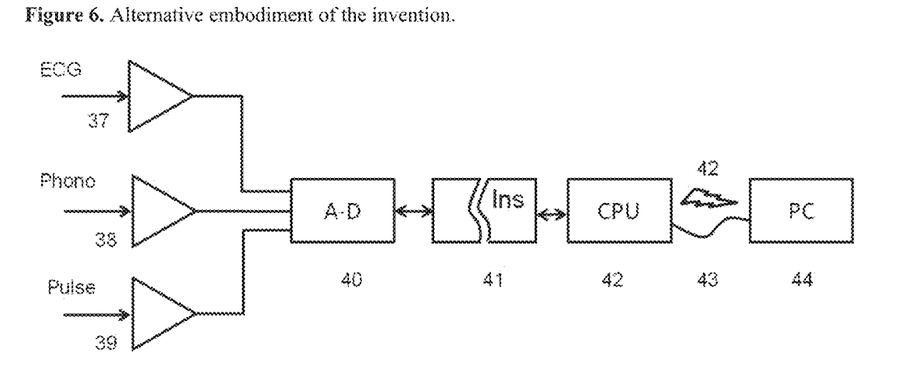

Another embodiment for this invention is shown in FIG. 6. ECG signal is amplified in 37, peripheral pulse in 38 and phonocardiogram in 39. Outputs of these amplifiers are fed to an analog to digital converter 40 connected to signal insulator 41 which also powers the A-D converter 40 and photo-plethysmograph 38. Digital signals are further processed in CPU 42, which feeds its output via USB or wireless 43 to a PC 44 where the analysis software resides.

Figure 7:
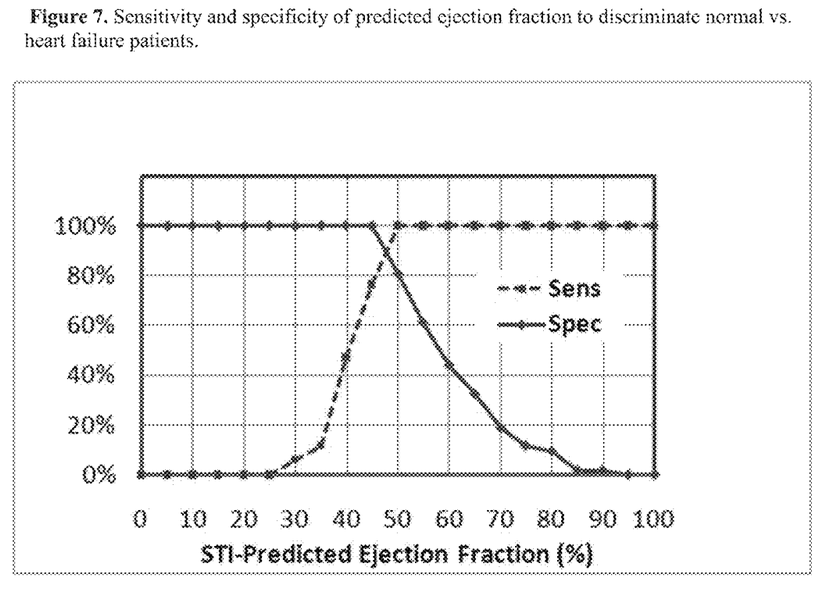

The prototype of this invention was tested in 69 patients with right ventricular pacing, 52 of them asymptomatic, with no cardiac malfunction and expected to have normal EF, and 17 with heart failure of various degrees, expected to have reduced EF. The ability of the ejection fraction predicted with the prototype of this invention to rule-in or rule-out cardiac malfunction is shown in FIG. 7. Using an EF cut-off point of 50% (lower limit of normal for ejection fraction obtained by other methods) sensitivity to detect heart failure was 100% and specificity 87%[7].

PRIOR ART PATENTS

| | | |
|---|---|---|
| Cormier | Jun. 13, 1978 | 4,094,308 |
| Cormier | Sep. 15, 1981 | 4,289,141 |
| Chirife | Jan. 19, 1988 | 4,719,921 |
| Weaver | Apr. 11, 1989 | 4,819,654 |
| Chirife | Sep. 12, 1989 | 4,865,036 |
| Fowler | Feb. 11, 1992 | 5,086,776 |
| Chirife | Oct. 13, 1992 | 5,154,171 |
| Chirife | Dec. 8, 1992 | 5,168,869 |
| Sackner | Jan. 12, 1993 | 5,178,151 |
| Stone | Dec. 13, 1994 | 5,372,607 |
| Hickey | Sep. 19, 2000 | 6,120,442 |
| Arand | Feb. 6, 2007 | 7,174,203 |
| Stahmann | Feb. 10, 2009 | 7,488,290 |
| Norèn | Aug. 4, 2009 | 7,569,020 |
| Osypka | Mar. 8, 2011 | 7,904,141 |
| Osypka | Oct. 22, 2013 | 8,562,538 B2 |
| Hirsh | Aug. 19, 2014 | 8,808,191 |

REFERENCES

1. Dodge H T, Sandler H, Ballew D W, Lord Jr J. D: The use of biplane angiocardiography for the measurement of left ventricular volume in man Am Heart J 1960; 60: 762-776
2. Bellenger N G, Marcus N J, Rajappan K, Yacoub M, Banner N R, Pennel D J: Comparison of Techniques for the Measurement of Left Ventricular Function Following Cardiac Transplantation. J Cardiovascr Magn Res 2002; 4: 255-263.
3. Bellenger N G, Burgess M I, Ray S G, Lahiri A, A. Coats A J S, Cleland J G F, Pennell D J: Comparison of left ventricular ejection fraction and volumes in heart failure by echocardiography, radionuclide ventriculography and cardiovascular magnetic resonance. Are they interchangeable? Eu Heart J 2000; 21:1387-1396.
4. Weissler A M, Harris W S, Schoenfeld C D: Systolic Time Intervals in Heart Failure in Man. Circulation 1968; 37:149-159
5. Chirife R, Spodick D H: Densitography: A new method for evaluation of cardiac performance at rest and during exercise. Amer. Heart J. 1972; 83:493
6. Guillian R E, Parnes W P, Ali Kahn M: The Prognostic Value of Systolic Time Intervals in Angina Pectoris Patients. Circulation 1979; 60:268-275
7. Chirife R, Ruiz A: Cardiac malfunction detected by systolic time intervals during right ventricular pacing. Heart Rhythm 2016; 13:S261
8. Spodick D H, Pigott V M, Chirife R: Pre clinical cardiac malfunction in chronic alcoholics. Comparison with matched normal controls and alcoholic cardiomyopathies. New Engl. J. of Med. 1972; 287:677.
9. Chirife R, Pigott V M, Spodick D H: Measurement of left ventricular ejection time by digital plethysmography. Amer. Heart J. 1971; 82:222.
10. Ambrosi C, Chabrillat Y, Duport G, Valeix B, Berthet-Bondet M, Gerard R Calculation of the ejection fraction from simultaneously recorded systolic intervals and angiography. Comparative study. Arch Mal Coeur Vaiss. 1981; 74:321-328.
11. Chirife R, Foerster J M, Bing O H L: Left ventricular ejection time by densitometry in patients at rest, during exercise, atrial pacing and atrial fibrillation: comparison with central aortic pressure measurements. Circulation 1974; 50:1200.
12. Chirife, R: The pre-ejection period: an ideal physiologic variable for rate responsive pacing. PACE 1987; 10:425.
13. Chirife R, Shapland J E, Salo R W, Ortega D F, Olive A L, Pederson B D: Behavior of the right ventricular pre-ejection period under cardiocirculatory challenges. Possible use of this interval to drive closed-loop rate responsive pacing systems. In: Belhassen B, Feldman S, Cooperman Y. Eds. "Cardiac Pacing and Electrophysiology", Tel-Aviv: Creative Comm. Ltd. 143, 1987.
14. Chirife R: Physiological principles of a new adaptive rate pacemaker controlled by pre-ejection interval. PACE, 1989; 11:1545
15. Cokkinos D V, Heimonas E T, Demopoulos J N, Harralambakis A, Tsartsalis G, Gardikas C D: Influence of heart rate increase on uncorrected pre-ejection period/left ventricular ejection time (PEP/LVET) ratio in normal individuals. Heart 1976; 38:683-688.
16. Garrard C L, Weissler A M, Dodge H T: The Relationship of Alterations in Systolic Time Intervals to Ejection Fraction in Patients with Cardiac Disease. Circulation, 1970 42:455-462
17. Reant P, Dijos M, Donal D, Mignot A, Ritter P, Bordachar P, Dos Santos P, Leclercq C, Roudaut R, Habib G, Lafitte S: Systolic time intervals as simple echocardiographic parameters of left ventricular systolic performance: correlation with ejection fraction and longitudinal two-dimensional strain. Eur J of Echocard 2010; 11:834-844.
18. Cokkinos D V, Christoulas S, Trapalis C, Ioannou N, Diakoumakos N, Drakotos A, Edelman S K: New criteria to increase the reliability of systolic time intervals in left bundle branch block and right ventricular pacing. Acta Cardiol. 1988; 43:583-594
19. Chirife R (on behalf of the Latin America CRT Study): Prediction of left ventricular ejection fraction from systolic time intervals in patients with left bundle branch block. Europace 2016; 18:216
20. Chirife R, Pastori J, Mosto H, Arrascaite M, Sambelashvili A: Prediction of Interatrial and Interventricular Electromechanical Delays from P/QRS Measurements: Value for Pacemaker Timing Optimization. PACE 2008; 31:37-43

The invention claimed is:

1. A device for automatic measurement of systolic time intervals, including heart rate (HR), QRS duration, a surrogate of left ventricular pre-ejection period (PEPsu), left ventricular ejection time (LVET), inter-ventricular delay (IVD) and pulse transit time (PTT) allowing automatic detection and display of corrected systolic time intervals, the calculation of a systolic function index, and estimation of left ventricular ejection fraction in patients with narrow QRS, bundle branch block and artificial cardiac pacing, wherein the device comprises:
   a. amplifiers and filters for each of: ECG, arterial pulse and phonocardiogram,
   b. a first timer for the onset of QRS or ventricular pacing pulse, whichever is first to occur,
   c. a second timer for detecting end of QRS,
   d. a third timer for the upstroke of the arterial pulse,
   e. a fourth timer for the dicrotic notch of the arterial pulse (Tnotch),
   f. a fifth timer for detecting aortic component of the second heart sound (TS2A),
   g. a processor unit for running software for:
   calculating a beat to beat heart rate,
   calculating QRS duration (QRSd),
   calculating rate-corrected LVET as:

$LVETc = LVET + k*(HR-60)$, wherein k is a value between 1.0 and 2, which can be defaulted as 1.5 or calculated as the ratio delta LVET/delta HR,
   calculating of inter-ventricular delay caused by bundle branch block and/or cardiac pacing, as:

$IVD = 0.38*QRSd - 8$, calculating PTT as:

$Tnotch - TS2A$ obtaining a corrected PEP as:

$PEPc = PEPsu - PTT - IVD$, wherein PTT=0 for central pulse recordings
   calculating a systolic function index as:

$SFI = LVETc/PEPc$, calculating a left ventricular ejection fraction (EF) as:

$EF = (0.45*LN(SFI) - 0.03)*100$, wherein LN(SFI) is the natural logarithm of the SFI.

2. The device according to claim 1, wherein said systolic time intervals and said systolic function index and ejection fraction are obtained as integral part of an implantable medical device such as a pacemaker, cardiac defibrillator, monitoring device or drug infusion apparatus.

3. The device according to claim 1, wherein said ECG, pulse and phonocardiogram amplifiers, filters are the integral part of a system including analysis, calculation software and display means.

4. The device according to claim 1 wherein said ECG, pulse and phonocardiogram amplifiers, filters, are connected via USB, Bluetooth or other transmission means to a computer running the software for measurement and calculations of said systolic time intervals, heart rate, corrections of PEP, corrections of LVET, systolic function index and ejection fraction.

5. A device as described in claim 1 wherein said parameters of cardiac performance are used for diagnosis, automatic adjustment of medical devices, such as home monitoring, arrhythmia detection, device optimization, drug delivery, rate adaptive pacing, pacing mode selection and/or atrio-ventricular interval optimization in pacemaker patients.

6. A device and method as described in claim 2 wherein said parameters of cardiac performance are used to trigger an alarm when one or more of said detected parameters exceed a pre-selected or programmable risk level.

* * * * *